(12) United States Patent
Ruysschaert et al.

(10) Patent No.: US 6,613,351 B1
(45) Date of Patent: Sep. 2, 2003

(54) COMPOUND CAPABLE OF INTRODUCING AT LEAST ONE MOLECULE INTO A CELL

(75) Inventors: Jean-Marie Ruysschaert, Brussels (BE); Robert Fuks, Brussels (BE); Michel Vandenbranden, Brussels (BE)

(73) Assignee: Biotech Tools S.A., Brussels (BE)

( * ) Notice: Subject to any disclaimer, the term of this patent is extended or adjusted under 35 U.S.C. 154(b) by 0 days.

(21) Appl. No.: 09/150,976

(22) Filed: Sep. 11, 1998

Related U.S. Application Data

(63) Continuation-in-part of application No. 08/663,294, filed as application No. PCT/BE94/00096 on Dec. 19, 1994, now abandoned, and a continuation-in-part of application No. 08/170,124, filed on Dec. 20, 1993, now abandoned.
(60) Provisional application No. 60/058,636, filed on Sep. 12, 1997.

(51) Int. Cl.$^7$ .......................... A61K 9/127; C07H 21/04; C07K 17/00
(52) U.S. Cl. ...................... 424/450; 536/23.1; 530/350
(58) Field of Search ........................ 424/450; 435/458; 530/350; 536/23.1

(56) References Cited

U.S. PATENT DOCUMENTS

| | | | |
|---|---|---|---|
| 4,897,355 A | * | 1/1990 | Eppstein et al. ............ 424/450 |
| 5,264,618 A | * | 11/1993 | Felgner et al. .............. 560/224 |

FOREIGN PATENT DOCUMENTS

| WO | WO 91/15501 | 10/1991 |
|---|---|---|

OTHER PUBLICATIONS

Defrise–Quertain et al (J. Chem. Soc. Commun. 14: 1060–1062, Jul. 1986.*

Patterson et al (Eur. J. Cancer Clin. Oncol. 25(S63–68, Supplement, 2, 1989.*

J–Y Legendre et al., Pharmaceutical Research, "Delivery of Plasmid DNA into Mammalian Cell Lines Using pH Sensitive Liposomes:Comparison with Cationic Liposomes," 1992, vol. 9, No. 10, pp. 1235–1242.*

Straubinger, R.M. (1987) pH–Sensitive Liposomes for Delivery of Macromolecules into Cytoplasm of Cultured Cells. Methods and EnzyNology 221: p. 361–376.

El Quahabi, Al., et al. (1997) The role of endosome destabilizing activity in the gene transfer process mediated by catIonic lipids. FEBS Letters 414 p. 187–192.

Pector, V., et al., (1998) Physico–chemical characterization of a double long–chain cationic amphiphile (Vectamidine) by microelectrophoresis. BiochIm. Biophys. Acta. 1372:339–346.

Defrise–Quertain, F., et al. (1986) Vesicle Formation by Double Long–chain Amidines. J. Chem Soc. Chem. Commun. pp. 1060–1062.

Patterson, T.F., et al. (1989) The Role of Liposomal Amphotericin B in the Treatment of Systemic Fungal Infections. Eur J. Cancer Clin. Oncol. vol. 25, Supp. 2. p. S63–S68.

Düzgünes, N. (1985) Membrane fusion. Subcell Biochem 11:195–286.

Felgner, P.L., et al. (1987) Lipofection: A highly efficient, lipid–mediated DNA–transfection procedure. Proc. Natl. Acad. Sci. 84: 7413–7417.

* cited by examiner

*Primary Examiner*—Jeffrey Siew
*Assistant Examiner*—Richard Schnizer
(74) *Attorney, Agent, or Firm*—Merchant & Gould P.C.

(57) ABSTRACT

The invention includes a vector including a complex between at least one compound having an amidine polar head of formula

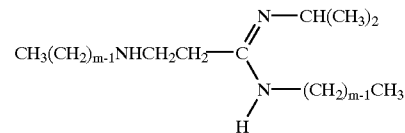

where m is 14 and at least one of nucleic acids molecules, polypeptides, and glycosylated polypeptides.

2 Claims, 1 Drawing Sheet

US 6,613,351 B1

COMPOUND CAPABLE OF INTRODUCING AT LEAST ONE MOLECULE INTO A CELL

This application is a continuation-in-part of U.S. application Ser. No. 08/663,294, filed Sep. 9, 1996, now abandoned which is the U.S. national phase under 35 U.S.C. §317 of International Application PCT/BE94/00096, filed Dec. 19, 1994, and is a continuation-in-part of U.S. application Ser. No. 08/170,124 filed Dec. 20, 1993, now abandoned. This application also claims priority under 35 U.S.C. §119(e) from U.S. Provisional Application No. 60/058,636, filed Sep. 12, 1997.

FIELD OF THE INVENTION

The invention relates to a compound capable of introducing at least one molecule into a cell.

The invention also relates to a positively charged vesicle whose membrane comprises this compound, to a vector containing at least one molecular combined with the vesicle according to the invention; to the cell, animal and/or plant transformed by said compound or said vector as well as to the pharmaceutical or cosmetic composition, comprising said vector and/or the cell transformed by said vector.

The invention also relates to the process for the synthesis of said compound and to the process for the production of said vector.

Another aspect of the invention relates to the use of the compound and/or vector for the introduction in vitro and/or in vivo of at least one molecule into a cell.

TECHNOLOGICAL BACKGROUND AND PRIOR STATE OF THE ART WHICH FORM THE BASIS OF THE INVENTION

Various processes are used in genetic engineering and/or in pharmacy to introduce molecules such as nucleic acids or active therapeutic agents into cells.

Transfection is a method which is widely used for introducing genetic material into cells, for studying the expression of genes, and for developing strategies for gene therapy.

Numerous experimental procedures using physical modifications (microinjection, electroporation and the like) or chemical modifications (dextran phosphate, calcium phosphate and the like) of membranes have been developed with varying success for introducing nucleic acids into cells using this method.

Another axis of research relates to the development of new amphiphilic cationic vectors which have demonstrated their effectiveness and their ease of use for causing the genetic material to penetrate into cells in vitro (P. L. Felgner et al., Proc. Natl. Acad. Sci., USA, 84, pp. 7413–7417 (1987)).

Some of these vectors such as the Lipofectin® N-(2,3-dioleyloxy)propyl-N,N,N-trimethylammonium chloride (DOTMA) from GIBCO BRL or the Transfection-reagent® N-(2,3-dioleoyloxy)propyl-N,N,N-trimethylammonium methyl sulfate (DOTAP) from Boehringer Mannheim GmbH, have been commercialized.

Patent Application WO91/15501 (YALE UNIVERSITY) also describes a positively charged reagent consisting of a neutral phospholipid such as dioleoylphosphatidylethanolamine and a cationic lipid such as stearylamine, a tertiary amine or a benzothorium salt for the transfection of nucleic acids.

Nevertheless, these products require large quantities of reagents in order to obtain an effective transfection of cells and therefore increase the cytotoxicity of the products and their costs (thus, the price of the "Lipofectin®" product (DOTMA) in U.S.$ 145/ml, equivalent to U.S. $10 per transfection).

In addition, Lipofectin® (DOTMA) has the additional disadvantage of not being capable of being added to a serum.

The document "Vesicle Formation by double long-chain Amidines" (Fabienne Defrise-Quertain et al.) (J. Chem. Soc., Chem. Commun., 1986, p. 1060 to 1062) describes the formation of vesicles consisting of 3-tetradecylamino-N-tert-butyl-N'-tetradecylpropionamidine.

However, this document does not contain sufficient description for the preparation of these compounds. Indeed, this document does not indicate the reaction temperatures to be used or the fact that it is necessary to use a basic aqueous solution in order to form the compound of formula $$CH_2=CHC\begin{smallmatrix}\nearrow NR^2\\ \searrow OR\end{smallmatrix}$$

in which OR is the residue of an alcohol of formula ROH and $R^2$ is selected from the group consisting of hydrogen atom, saturated alkyl chains, unsaturated alkyl chains and substituted alkyl chains; an intermediate compound which is necessary for the production of the compounds according to the invention.

AIMS OF THE INVENTION

The aim of the present invention is to produce a new compound and/or a new vector capable of introducing at least one molecule into a cell, without exhibiting the disadvantages of the prior state of the art.

The invention is also intended for producing a pharmaceutical or cosmetic composition comprising said vector and/or said cell transformed by said vector.

An additional aim of the present invention is intended for producing a vector which can be used in a serum.

CHARACTERISTIC ELEMENTS OF THE INVENTION

The present invention relates to a compound of the general formula:

$$A-(CH_2)_{\overline{n}}-C\begin{smallmatrix}\nearrow N-R^2\\ \searrow N-R^3\\ \phantom{\searrow N-}R^4\end{smallmatrix}$$

in which:

A is selected from the group consisting of the radicals comprising a hydrophilic group or a $CH_2$ group and a hydrophobic group;

n is a positive integer (1<n<10; more preferably n=2); and $R^2$, $R^3$ and $R^4$ are selected from the group consisting of a hydrogen atom, saturated alkyl chains, unsaturated alkyl chains and substituted alkyl chains.

Preferably, A represents a radical or residue of formula:

$$R^1-X-$$

in which
R$^1$ is selected from the group consisting of a hydrogen atom, saturated alkyl chains, unsaturated alkyl chains and substituted alkyl chains, and
X represents a divalent atom or a divalent group of atoms.
R$^1$—X represents a residue selected from the group consisting of:

$$R^1-CH_2-; \quad R^1-\overset{O}{\underset{\|}{C}}-; \quad R^1-O-; \quad R^1-\overset{O}{\underset{\|}{C}}-O-;$$

$$R^1-O-\overset{O}{\underset{\|}{C}}- \quad R^1-S-; \quad R^1-\overset{\|}{\underset{\|}{S}}-; \quad R^1-\overset{O}{\underset{\underset{O}{\|}}{\overset{\|}{S}}}-;$$

$$R^1-S-\overset{O}{\underset{\|}{C}}-; \quad R^1-\overset{O}{\underset{\|}{C}}-S-; \quad R^1-O-\overset{O}{\underset{\underset{O}{\|}}{\overset{\|}{S}}}-O-;$$

$$R^1-O-\overset{O}{\underset{\underset{O}{\|}}{\overset{\|}{S}}}-; \quad R^1-\overset{O}{\underset{\underset{O}{\|}}{\overset{\|}{S}}}-O-$$

Preferred compounds according to the invention are the nitrogen derivatives above-described.

Advantageously, R$^1$ and R$^3$ or R$^1$ and R$^4$ are selected from the group consisting of hydrocarbon chains containing 2 or more carbon atoms, preferably 12, 14, 16 or 18 carbon atoms chains.

According to a preferred embodiment of the invention, the compound according to the invention corresponds to the following formula:

$$CH_3(CH_2)_{m-1}X-(CH_2)_2-C\underset{NH(CH_2)_{m-1}CH_3}{\overset{N=C(CH_3)_3}{\diagup}}$$

in which $12 \leq m \leq 18$ (m=12, 14, 16 or 18), and X represents the divalent atoms or divalent groups of atoms above-described.

According to another preferred embodiment of the present invention, the compound according to the invention has the following formula:

$$CH_3(CH_2)_{m-1}NHCH_2CH_2-C\underset{NH(CH_2)_{m-1}CH_3}{\overset{N=CH(CH_3)_2}{\diagup}}$$

wherein m=12, 14, 16 or 18.

The invention also relates to a positively charged vehicle having a membrane comprising a compound according to the invention as well as a vector consisting of said vesicle associated with at least one molecule to be introduced into a cell, said molecule being advantageously selected from the group consisting of nucleic acids (nucleic acids oligomers or nucleic polymers), antigens, polypeptides or optionally glycosylated proteins and/or active therapeutic or cosmetic agents.

Said molecule is introduced in a cell by a process wherein said cell is brought into contact with said molecule and a compound and/or a vesicle according to the invention. Likewise, the introduction process can be achieved by bringing said cell into contact with a vector according to the invention.

A "nucleic acid according to the invention" means any kind of nucleic acids polymer of oligomer such as a plasmid, messenger RNAs, antisense RNAs, cDNAs, synthetic oligonucleotides and the like which are capable of genetically transforming a cell and which may express a specific antigen, polypeptide or protein as well as an active therapeutic or cosmetic agent into said cell.

According to a first embodiment of the process of the invention, a cell is treated in vitro in order to produce plants or animals which are transgenic or for gene therapy, in particular for the treatment of cellular disorders such as cancer or infections such as viral or bacterial infections or the like.

According to the second preferred embodiment of the process of the invention, a cell is treated in vivo in order to produce recombinant microorganisms, plants and/or animals which are transgenic or in for ex vivo or in vivo gene therapy.

Another aspect of the invention concerns a new composition comprising a molecule to compact DNA, preferably a protamine, a polylysine or a histone derived peptide, and the compound, the vesicle or the vector according to the invention.

The composition according to the invention may also comprise another compound which increases cell endocytosis, preferably a microtubule inhibitor.

Another aspect of the present invention is related to a transfection kit comprising said composition, compound(s), vesicle or vector according to the invention, for the transfection of cells, plants or animals.

The present invention also relates to the cell, the animal or the plant transformed by the vector according to the invention as well as a cosmetic or pharmaceutical (such as a vaccine) comprising the vector and/or the transformed cell according to the invention.

Another aspect of the present invention relates to the process for the synthesis of the compound in which compounds of formula $CH_2=CHC=N$ and $R^2-Cl$ are reacted with anhydrous ferric chloride so as to form the tetrachloroferrate of a compound of formula $CH_2=CHC=N^+-R^2$, this tetrachloroferrate is treated with an amine of formula $R^3-NH-R^4$ so as to form a compound of formula:

$$\underset{R^4}{\overset{R^3}{\diagdown}}N-CH_2-CH_2-C\underset{\underset{R^4}{\overset{N-R^3}{\diagdown}}}{\overset{N=R^2}{\diagup}}$$

The invention also relates to a process for the production of the vector according to the invention in which at least one molecule selected from the group consisting of nucleic acids molecules, antigen molecules, polypeptides, glycosylated polypeptides, proteins, glycosylated proteins, therapeutic agents and cosmetic agents are reacted with a vesicle according to the invention.

A final aspect of the present invention relates to the use of the vector and/or the compound according to the invention for the introduction of one or more molecules into a cell in vitro as well as the use of the vector according to the invention for the introduction of one or more molecules into a cell in vivo.

Figure 2:
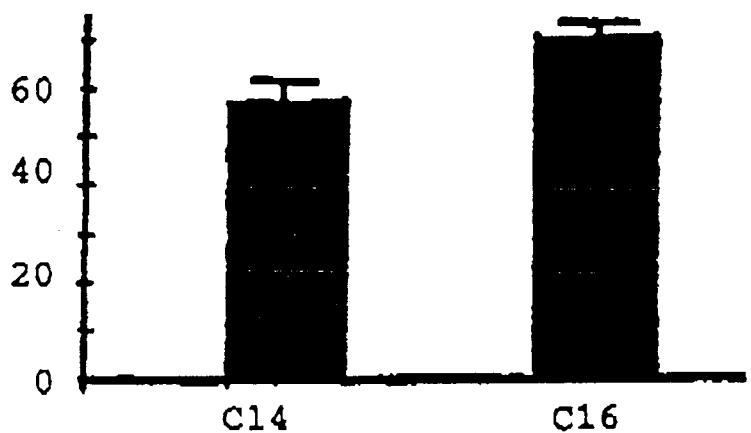

FIG. 2 illustrates transfection activity (in β-galactosidase units) of HEK293 cells using 3-tetradecylamino-N-isopropyl-N'-tetradecylpropionamidine (dented C14 on the figure) and 3-hexadecylamino-N-isopropyl-N'-hexadecylaminopropionamidine (denoted C16 on the figure) at 6:1 agent/DNA weight ratios.

Figure 3:
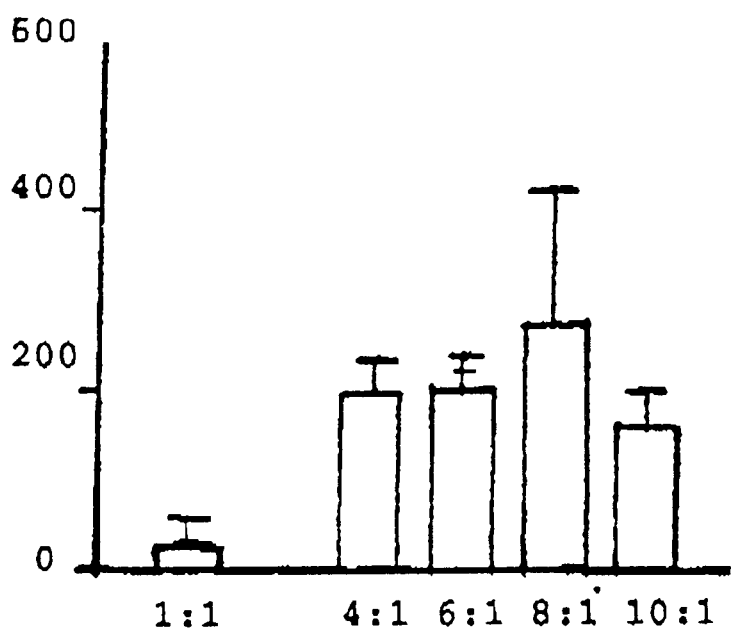

FIG. 3 illustrates transfection activity (in β-galactosidase units) of COS cells using 3-tetradecylamino-N-isopropyl-N'-tetradecylpropionamidine at different agent/DNA weight ratios.

DESCRIPTION OF A PREFERRED EMBODIMENT OF THE INVENTION

The present invention is based on the unexpected fact that a compound of general formula:

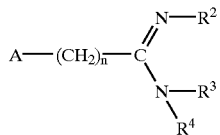

in which:

A is selected from the group consisting of the radicals comprising a hydrophilic group or a $CH_2$ group and a hydrophobic group;

n is a positive integer (n<1, preferably n=2), $R^2$, $R^3$ and $R^4$ are selected from the group consisting of a hydrogen atom, saturated alkyl chains, unsaturated alkyl chains and substituted alkyl chains, can form vesicles and combine with other molecules to form a vector capable of introducing said molecules into an animal or plant cell or a microorganism.

By "other molecules" there is understood any molecular structure such as nucleic acids molecules, antigen molecules, polypeptides, glycosylated polypeptides, proteins, glycosylated proteins, therapeutic agents and cosmetic agents, capable of modifying the state of said cell, in particular the physico-chemical state or the genome of said cell.

EXAMPLES

Example 1

Synthesis of 3-alkylamino-N-isopropyl-N'-alkyl-propionamidine (6)

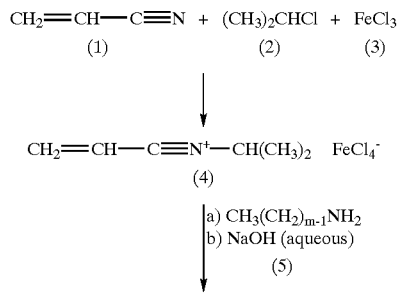

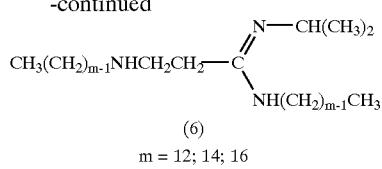

m = 12; 14; 16

Acrylonitrile is converted to a nitrilium salt 4, which treated "in situ" with the alkylamine 5 gives in all cases the double-long-chain amidine 6 with yields depending on the chain length (see Table 1).

The following experimental procedure was used: 6.6 ml (0.1 mol) of acrylonitrile was added to 16.2 g (0.1 mol) of ferric chloride in 100 ml of isopropyl chloride cooled with an ice bath. The mixture was stirred under nitrogen for 1.5 hours. Excess isopropyl chloride was evaporated under vacuum. The residue, as represented by structure (4) was taken up in 100 ml of dichloromethane and the mixture was cooled at −10° C. Amine (5) (0.1 mol) in 150 ml of dichloromethane was added with stirring. After this addition, the mixture was kept overnight at room temperature with stirring. The mixture was then poured on 500 ml of 1.5 M aqueous sodium hydroxide cooled at 0° C. The mixture was then separated after settling has taken place at room temperature. The aqueous phase is extracted twice with 100 ml of dichloromethane. The combined organic phases are dried over magnesium sulfate and then filtered. Evaporation of the solution gave the crude double long chain amino-amidine (6). It is taken up in hexane and filtered on a γ-Tonerde alumiuna column. The filtrate is evaporated under vacuum and the residue crystallised from hexane in the refrigerator. It is recrystallised in the same solvent (see Table 1).

TABLE 1

Synthesis of 3-alkylamino-N-isopropyl-N'-alkylpropionamidine (6)

| Alkylamine (5) | Hexane and $Al_2O_3$ | Yield in amidine (6) after 4 crystallisations |
|---|---|---|
| m = 12 - 30.4 g - 0.164 mol | 50 ml - 200 g | 2.1 g - 9% |
| m = 14 - 35.0 g - 0.164 mol | 50 ml - 200 g | 3.1 g - 14% |
| m = 16 - 39.6 g - 0.164 mol | 50 ml - 200 g | 1.8 g - 6% |

The physical, spectroscopic and analytical characteristics are given in Table 2.

TABLE 2

Physical, analytical and spectroscopic data of amidines (6) (Example 1)

| amidine (6) | m.p. (° C.)a | Molecular formula M | Mass spectrum M+ | $^1$H NMR (CDCl$_3$; 250 MHs) |
|---|---|---|---|---|
| m = 12 | 27–28 | $C_{30}H_{63}N_3$ 465.85 | 465 | 3.73(1H, s); 3.13(2H, s); 2.79 (2H, t) 2.58(2H, t); 2.35(2H, t); 1.47 (4H, m) 1.26(36H, s); 1.10(6H, d); 0.88(6H, t) |
| m = 14 | 29.5–30.5 | $C_{34}H_{71}N_3$ 521.96 | 521 | 3.73(1H, s); 3.14(2H, s); 2.79(2H, t) 2.58(2H, t); 2.34(2H,t); 1.47(4H, m) 1.26(44H, s); 1.10(6H, d); 0.88(6H, t) |

TABLE 2-continued

Physical, analytical and spectroscopic data of amidines (6) (Example 1)

| amidine (6) | m.p. (° C.)[a] | Molecular formula M | Mass spectrum M+ | $^1$H NMR (CDCl$_3$; 250 MHs) |
|---|---|---|---|---|
| m = 16 | 39.5–40.5 | C$_{38}$H$_{79}$N$_3$ 578.06 | 577 | 3.74(1H, s); 3.14(2H, s); 2.78 (2H, t) 2.58(2H, t); 2.34(2H, t); 1.46(4H, m) 1.26(52H, s); 1.10(6H, d); 0.88(6H, t) |
| m = 18 | 49–50 | C$_{42}$H$_{87}$N$_3$ 634.18 | 634 | — |

Example 2

Synthesis of 3-alkylamino-N-tert-butyl-N'-alkyl-propionamidine (8)

$$CH_2 = CHC \equiv N + (CH_3)_3CCl + FeCl_3$$
$$\quad\quad 1 \quad\quad\quad\quad 2 \quad\quad\quad 3$$

$$CH_2 = CH - C \equiv N^+ - C(CH_3)_3 \; FeCl_4^-$$
$$(4)$$

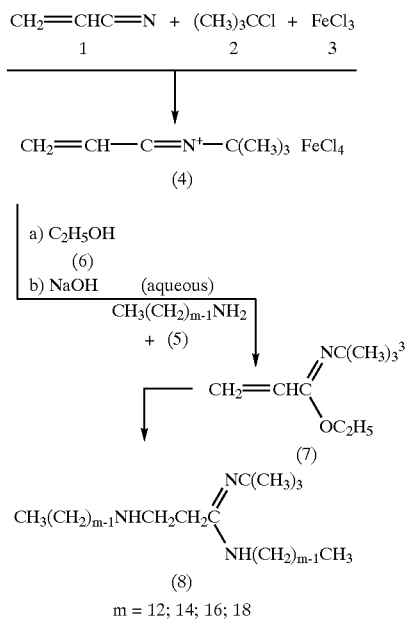

(8)

m = 12; 14; 16; 18

Acrylonitrile is converted to a nitrilium salt 4, which is treated "in situ" by ethanol 6 to ethyl N-tert-butylpropenimidate 7, a colorless liquid which is stable at cold temperature (refrigerator) for several weeks. Nevertheless, left at room temperature, compound 7 becomes slowly degraded by polymerization. The imidate 7 (1 equivalent), treated with the alkylamine 5 (2 equivalents) at 65° C., gives in all cases the double-long-chain amidine 8 with yields of 60–65% (see Table 3).

To a stirred suspension of 65 (0.4 mol) of anhydrous ferric chloride in 300 ml of anhydrous dichloromethane at −25° C., are added 28 ml (0.42 ml) of acrylontrile 1. After 5 minutes, the red suspension is cooled to −35° C. and 46 ml (0.42 ml) of tert-butyl chloride (2) are then added. The color passes from red to ochre thus forming N-tert-butylacrylonitrilium tetrachloroferrate (4). The suspension is cooled to −80° C. and 46.8 g (10.8 mol) of absolute ethanol (dried and distilled over magnesium) are added thereto, with stirring. The temperature of the mixture is allowed to rise up to −20° C. and then it is added to 800 ml of 1.5 M aqueous sodium hydroxide cooled to 0° C. The mixture is then separated after settling has taken place at room temperature. The aqueous phase is extracted 3 times with 100 ml of dichloromethane. The combined organic phases are dried over magnesium sulfate and then filtered. After addition of a spatula-tip quantity of hydroquinone, the solution is evaporated using a rotary evaporator, the bath should not exceed 30° C. The liquid residue is then distilled under vacuum on a small column provided with a dephlegmator at 56° C. under 30 torr. Yield 41.01 g, equivalent to 66% of 7.

A suspension of 2 equivalents of alkylamine 5 in 1 equivalent of acrylimidate 7 is stirred under vacuum produced by a water-jet pump and heated to 65° C. After 6 h, the mixture is allowed to cool. It is taken up in hexane and filtered on an γ-Tonerde alumina column. The filtrate is evaporated under vacuum and then pump-dried, with stirring, and by melting and solidifying the amidine 8 several times (see Table 3).

TABLE 3

Synthesis of 3-alkylamino-N-tert-butyl-N'-alkylpropionamidine 8 from ethyl N-tert-butylacylimidate 7

| Alkylamine 5 | Acrylimidate 2 | Hexane and Al$_2$O$_3$ | Yield |
|---|---|---|---|
| m = 12; 18.5 g (0.1 mol) | 7.75 g (0.05 mol) | 50 ml; 200 g | 15.47 g; 65% |
| m - 14; 21.3 g (0.1 mol) | 7.75 g (0.05 mol) | 50 ml; 200 g | 17.82 g; 66% |
| m = 16; 19.28 g (0.08 mol) | 6.2 g (0.04 mol) | 60 ml; 160 g | 14.6 g; 62% |
| m = 18; 21.5 g (0.08 mol) | 6.2 g (0.04 mol) | 80 ml; 160 g | 15.69 g; 61% |

The physical, spectroscopic and analytical characteristics are given in Table 4.

TABLE 4

Physical, Analytical and Spectroscopic data of amidines (8)

| amidine (8) | m.p. ° C. (a) | Molecular formulae (M) | Elementary analysis (b) calculated (%) | found (%) | Mass Spectra (c) M+ |
|---|---|---|---|---|---|
| m = 12 | 27–29 | C$_{31}$H$_{65}$N$_3$ (479.85) | C 77.59 H 13.65 N 8.76 | 77.52 13.90 8.72 | 479 |
| m = 14 | 31–33 | C$_{35}$H$_{73}$N$_3$ (535.96) | C 78.43 H 13.73 N 7.84 | 78.13 14.10 7.72 | 535 |
| m = 16 | 37–39 | C$_{39}$H$_{81}$N$_3$ (592.06) | C 79.11 H 13.79 N 7.10 | 79.43 14.22 7.06 | 591 |
| m = 18 | 40–42 | C$_{43}$H$_{89}$N$_3$ (648.17) | C 79.68 H 13.84 N 6.48 | 79.62 14.05 6.57 | 647 |

(a) Determined on a Leitz Mikroskopheiztisch 350 and the m.ps. are not corrected
(b) Elementary analyses carried out at "Searl-Continental Pharma Laboratory"
(c) Determined on a Mass Spectrometer Hitachi RMU-6D

Example 3

Formation of Vesicles

The procedures for the formation of the vesicles are given for the two following compounds:

3-tetradecylamino-N-isopropyl-N'-tetradecylpropion-amidine (example 1, (6), m=14, vectamidine diC14-isop (1 mg/ml), and 3-hexadecylamino-N-isopropyl-N'-hexadecylpropion-
amidine, (example 1, (6), m=16, vectamidine diC16-
isop (1 mg/ml), which are hereafter referred to as
Vectamidine®.

Procedure 1

A solution of Vectamidine is prepared in ethanol (50 mg/ml). Dissolving is enabled by heating briefly at 55° C. Twenty microliters of this solution are rapidly injected, by means of a micropippet, into 1 ml of HBS buffer (10 mM Hepes, 150 mM NaCl, adjusted at pH 7.3 by addition of concentrated NaOH), heated to 55° C. During the operation, the solution is shaken on a vortex mixer. The resulting vehicle suspension (named "suspension") is incubated for an additional 1 minute at 55° C. and shaken again for 20 seconds on the vortex mixer. The suspension is allowed to cooled at room temperature (20° C.) before use. In a large number of experiments, the suspension was stored at 4° C. for several weeks but heating at 55° C. for 5 minutes and vortexing was necessary to restore the full transfecting activity.

Procedure 2

A solution of Vectamidine is prepared in ethanol (50 mg/ml). Dissolving is enabled by heating briefly at 55° C. If not used immediately, this solution is stored at −20° C. for better stability. Twenty microliters of this solution is placed in a 1 ml propylene tube and ethanol is completely evaporated under a stream of dried nitrogen. One ml of HBS buffer is added and the tube is heated at 55° C. for 5 minutes. Th tube is shaken vigorously on a vortex mixer for 20 seconds. The suspension is allowed to cool at room temperature (20° C.) before use.

Procedure 3

Formation of vesicles consisting of 3-tetradecylamino-N-tert-butyl-N'-tetradecylpropionamidine (pure $diC_{14}$-amidine-t-but (1 mg/ml)) (example 2)

A solution of vectamidine $diC_{14}$-t-but is prepared in ethanol (100 mg/ml). 30 µl (3 mg) of this solution are rapidly injected, by means of a Hamilton syringe, into 3 ml of Tris/HCl buffer (0.01 M, pH 7.4), heated to 30° C. During the operation, the solution is gently stirred by means of a magnetic bar. The vesicles form immediately.

Procedure 4

Formation of vesicles consisting of 3-tetradecylamino-N-tert-butyl-N'-tetradecylpropionamidine ((6) m-14) and phosphatidylethanolamine (vectamidine $diC_{14}$-t-but/PE (1 mg/ml)) (example 2)

1.25 mg of vectamidine $diC_{14}$-t-but and 1.75 mg of PE (bovine brain) dissolved in chloroform (10 mg/ml) are dried under a nitrogen stream so as to form a thin film on the walls of the tube; traces of the solvent are removed under vacuum overnight. The film is then mechanically stirred in the presence of 3 ml of Tris/HCl buffer (0.01 M, pH 7.4). The cloudy suspension obtained is then sonicated (Branson B-12 Sonifier, 60 W) under a nitrogen stream and on an ice bath until a clear suspension is produced (about 10 min).

Example 4

Transfection procedure Cell Lines

Transfection Procedures are given for the following cell lines: COS, CHO, BHK21, Hela, CV-1, NIH/3T3, HEK293.

Cells are mycoplasma-free, grow at their normal rate and show no morphological signs of degenerescence before use.

Transfection medium

The transfection medium is defined as Dulbecco Modified Eagle Medium (DMEM) (Life Technologies 41965-039), without serum, without antibiotics with 20 mM Hepes final conc. (from Hepes buffer, Life Technologies 15630-056).

DNA solution

DNA is a pCMV-lacZ plasmid DNA reporter system. Efficient transfection was also demonstrated using other reporter system including pCMV-cat, pEGFP-N1(Clontech).

Plasmid DNA is obtained by the techniques commonly used in a biotechnology laboratory: briefly, E. coli (DH5alpha or MM298) are transformed with the plasmid and grown in L. B. medium and plasmid purification is performed using the Qiagen kit (Qiagen) according the instructions of the manufacturer.

Purity and integrity of the plasmid is checked by absorbance measurement at 260 and 280 nm and agarose gel electrophoresis before use.

The final DNA solution is prepared by diluting plasmid DNA (from a 1 mg/ml stock solution in 10 mM Tris, 1 mM EDTA) in transfection medium to a concentration of 20 µg/ml.

Cell culture

Cells are routinely cultured in 75 $cm^2$ culture flasks (Orange Scientific, 2010200) in a cell incubator with 5% $CO_2$ and are passed every 2 days.

The day before the transfection, cells are briefly trypsinized (Trypsin-EDTA Life Technology 45300-027) and transfered to 96 well plates (Orange Scientific, ref 2030100) at 1–2× $10^4$ cells/well. Cell Status before transfection: 80% confluent after 24 hours culture.

Transfection medium

DMEM (Life Technologies 41965-039), without serum, without antibiotics with 20 mM Hepes final conc. (Life Technologies 15630-056).

Preparation of the Vectamidine solutions

Vectamidine/DNA ratio have been tested according to the following table.

| Vectamidine /DNA ratio | Volume of Vectamidine | Volume of transfection medium |
| --- | --- | --- |
| 1/1 | 5 microliters | 245 microliters |
| 2/1 | 10 microliters | 240 microliters |
| 3/1 | 15 microliters | 235 microliters |
| 4/1 | 20 microliters | 230 microliters |
| 6/1 | 30 microliters | 220 microliters |
| 8/1 | 40 microliters | 210 microliters |

The range shown in the table can be extended to other ratios if necessary.

Vectamidine/DNA complexes formation

For each Vectamidine/DNA ratio mentioned in the table here-above, combine 250 µl of the corresponding Vectamidine solution with 250 µl of DNA solution at 20 micrograms/ml in transfection medium into one sterile polystyrene tube and mix it gently but thoroughly.

Incubate the resulting Vectamidine/DNA complexes solution at room temperature for 15 min.

A few minutes before the Vectamidine/DNA complex formation is terminated, the medium was removed from the culture to be transfected and if cell adhesion is strong enough, the cells were washed with pre-warmed serum-free medium.

When the Vectamidine/DNA complexes are formed, dilute it 5 fold in transfection medium.

Gently aspirate the medium from culture vials and apply 100 microliters of the transfection solution onto the cells which have been grown in 96 wells plates.

Incubate culture plates at 37° C. in a $CO_2$ incubator for 30 min to 5 hours (2 to 3 hours were found optimal in most cases).

Completely remove the medium containing the transfection solution and replace with the complete medium recommended for the cell line under study. If cell adhesion is strong enough at this step, one can wash one time with complete medium. For suspended cells, proceed the washing step by centrifugation. Omitting this step and maintaining Vectamidine in culture medium after transfection may result in cell toxicity.

Culture cells in optimal conditions for growth and gene expression. For cells stopping growth while reaching confluence, cells are detached by trypsinization and transferred to larger dishes to allow optimal growth.

Transfection efficiency measurement procedure (example given for lacZ reporter gene)

After 48 hours culture in culture medium for gene expression, cell supernatants are discarded and cells are lysed in lysis buffer (see below) for 15 minutes at room temperature. The β-galactosidase activity using the OPNG from lacZ gene expression is measured using the OPNG colorimetric assay (see below).

Lysis buffer: 0.5% Triton X100 (Merck 11869) and 0.1% Na deoxycholate (Sigma D-6750)

ONPG assay in 96 wells microtiter plates:

Serial two fold dilutions of cell lysates are made (minimum 4 dil). To 50 μl of OPNG Mix are added and color development is monitored at 420 nm in a microtiter plate reader until color development. Avoid saturation. Keep protected from light between measurements. Reaction is terminated by the addition of 100 μl of 1M Na2CO3.

ONPG Mix (prepared before use): 0.2M Na phosphate pH 7.0 (analytical grade), 2 mM MgCl2 (analytical grade), 0.1M 2-mercaptoethanol (Sigma M-7154), 1.33 mg/ml ONPG (2-nitrophenyl-β-D-galactopyranoside, Boerhinger Mannheim 810088)

Standard curve: serial two fold dilutions of β-galactosidase (Boehringer Mannheim 105031, 1500 U/ml) first dilution: 125 mU/ml in lysis buffer, made before use.

Transfection of K562 cells (suspension cells)

The general protocol of transfection given above is used except that all the cell washing and medium replacement steps are performed by transferring the cells in conical polystyrene tubes for centrifugation and resuspension in the desired medium. The K562 cells are cultured at 1 million cells in a 4 cm diameter dish before transfection. Two ml Vectamidine/DNA complex containing 5 micrograms plasmid and from 5 to 40 micrograms of Vectamidine are required for transfection of each 4 cm diameter dish. One dish is required for every transfection compound/DNA ratio tested.

Transfection of HEK293 cells using 3-tetradecylamino-N-isopropyl-N'-tetradecylpropionamidine at different agent/DNA weight ratios indicated on the X-axis The standard transfection protocol described hereabove was followed.

Figure 1:
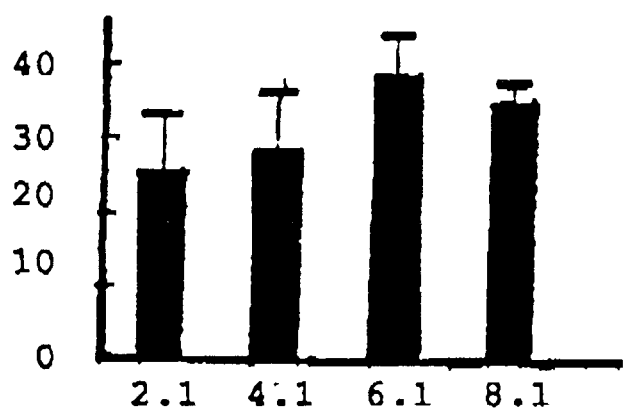
FIG. 1 illustrates transfection activity (in β-galactosidase units) of HEK293 cells using 3-tetradecylamino-N- isopropyl-N'-tetradecylpropionamidine at different agent/DNA weight ratios.

Transfection activity is indicated on the Y-scale (Beta-galactosidase units) of the FIG. 1.

Transfection of HEK-293 cells using 3-tetradecylamino-N-isopropyl-N'-tetradecylpropionamidine(denoted C14 on the figure) and 3-hexadecylamino-N-isopropyl-N'-hexadecylaminopropionamidine (denoted C16 on the figure) at 6:1 agent/DNA weight ratios The standard transfection protocol described hereabove was followed.

Transfection activity is indicated on the Y-scale (Beta-galactosidase units) of the FIG. 2.

Transfection of COS cells using 3-tetradecylamino-N-isopropyl-N'-tetradecylpropionamidine at different agent/DNA weight ratios indicated on the X-axis The standard transfection protocol described hreabove was followed.

Transfection activity is indicated on the Y-scale (Beta-galactosidase units) of the FIG. 3.

Formation of the vector vesicles-plasmid DNA

5 μg of plasmid DNA and 11 μg (11 μl) of pure $diC_{14}$-amidine suspension (for 25 μg (25 μl) of $diC_{14}$-amidine/PE suspension (see example 2)) are separately diluted in a final volume of 50 μl with distilled water and sterilized. Both solutions are then mixed and incubated for 15 min at room temperature.

Transfection of adherent cells

The cells are cultured in 6-well culture dishes until they are 80–90% confluent.

The suspension containing the complex ($diC_{14}$-amidine-DNA or $diC_{14}$-amidine/PE-DNA) is gently mixed with 2 ml of culture medium. The culture medium used for the transfection operation is identical to the usual culture medium for the cells to be transformed. The medium is prepared with 2.5% or without serum.

The mixture thus formed constitutes the "transfection medium". The cells (about $10^6$) are washed with the culture medium and the transfection medium is added. The medium is incubated for the desired period. This period may depend on the cell line to be transfected but an incubation time of 2–3 h is generally used. After incubation, the transfection medium is replaced with fresh medium; 6 hours later, the cells can be transfected into 100 mm culture dishes.

Transfection of cells in suspension

The suspension containing the complex ($diC_{14}$-amidine-DNA or $diC_{14}$-amidine/PE-DNA) is gently mixed with 10 ml of medium. The mixture thus formed constitutes the "transfection medium". Aliquots of $10^6$ cells are centrifuged and the pellets are resuspended in the transfection medium. The cell suspensions are distributed into 100 mm culture dishes. The suspensions are incubated for the desired period; after incubation, the cells are centrifuged and resuspended in 10 ml of fresh medium and then cultured normally.

CHO (Chinese Hamster Ovary) cells are cultured in F12 medium supplemented with 1% glutamine and 1% penicillin/streptomycin and containing 10% FCS (Fetal Calf Serum, K562 (human myeloid) cells are cultured in RFMI medium supplemented with antibiotics and non-essential amino acids and containing 10% FCS (0.5–1×$10^6$ cells/ml). Both cell lines are cultured under a $CO_2$ atmosphere (37° C., 5% $CO_2$).

The plasmid used is derived from the commercial plasmid pCMV5 into which the bacterial replication origin S1, the ampicillin resistance gene and the CAT gene of bacterial origin have been inserted. It is approximately 5000 base pairs in size and is stored at a concentration of 1 mg/ml.

The general procedure described above was followed; 5 μg (5 μl) of plasmid DNA and 11 μg (11 μl) of pure $diC_{14}$-amidine suspension (or 25 μg (25 μl) of $diC_{14}$-amidine/PE suspension) prepared as described above are used. The CHO cells (adherent) are plated in the 6-well culture dishes the day before the experiment in an amount of $10^6$ cells/well; while the K562 cells (in suspension) are used in an amount of $10^6$ cells per experiment.

The incubation was carried out for 3 h for the two cell lines. The transfection medium is the normal culture medium (with serum) with which vesicle vector (pure $diC_{14}$- amidine or diC$_{14}$-amidine/PE/DNA) has been mixed under the conditions described in the general procedure.

After incubation, the cells are treated as described above; the CHO cells are transferred after 6 h into 100 mm culture dishes. The two cell lines continue to grow for 36 h before the CAT assay performed as described by Gorman et al., B.H. (1982), Mol. Cell. Biol. 2, 1044–1051; in brief, the cell lysates are incubated at 37° C. with [$^{14}$C]chloramphenicol and acetyl CoA for 2 h and extracted with ethyl acetate. The organic phase is eluted by TLC (thin-layer chromatography) with chloroform/methanol 95:5. The acetylation of chloramphenicol is determined by autoradiography on the chromatograms and counting of the spots on the plate.

Table 5 below gives the comparison of the transfection efficiency of the CAT gene for diC$_{14}$ and the product DOTAP® marketed by Boehringer Mannheim, expressed as percentage of acetylated chloramphenicol in the cellular extract, under identical experimental conditions.

The cell lines of this example are CHO cells (adherent cells) and K562 cells (suspension cells).

The composition of the vector comprises: μg quantities of plasmid DNA and μg quantities of cationic vesicles.

TABLE 5

| Composition of vector | Adherent cells | | Suspension cells | |
| --- | --- | --- | --- | --- |
| | diC$_{14}$-t-but | DOTAP | diC$_{14}$-t-but | DOTAP |
| 2 + 5 (μg) | 63% | 32% | 60% | 29% |
| 5 + 10 (μg) | 65% | 40% | 68% | 36% |

The diC$_{14}$-t-but allows transfection efficiencies with quantities two to three times lower than the available commercial products, namely DOTAP® from Boehringer Mannheim and Lipofectin® from Gibco BRL; in addition, the transfection efficiency advantageously limits the cytotoxicity of the product used.

Transfection of genetic material

100 μg of BLV (Bovine Leukemia Virus) genome and 200 μg of amidine C14 (vector as prepared according to the protocol above-described) were hypodermically injected into a sheep. After 1 month, the corresponding virus envelope protein (51 kD) is detected immunochemically in the sheep's serum.

This unexpected result shows clearly that the vector according to the invention is advantageously applied in vivo and could be used in the field of gene therapy or for the creation of new genetically modified plants or animals.

What is claimed is:

1. A vector comprising a complex between (a) at least one compound having an amidine polar head of formula:

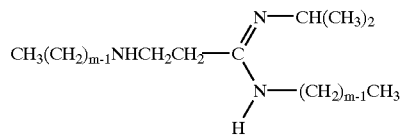

wherein m=14; and (b) at least one molecule selected from the group consisting of nucleic acid molecules, polypeptides, and glycosylated polypeptides.

2. A vector comprising a complex between (a) at least one compound having an amidine polar head of formula:

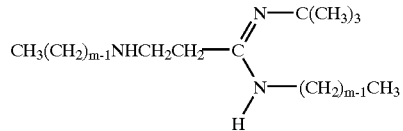

wherein m=14; and (b) at least one molecule selected from the group consisting of nucleic acid molecules, polypeptides, and glycosylated polypeptides.

* * * * *